(12) United States Patent
DiLeo

(10) Patent No.: US 8,137,983 B2
(45) Date of Patent: *Mar. 20, 2012

(54) METHOD OF MAINTAINING A PROTEIN CONCENTRATION AT A TANGENTIAL FLOW FILTER

(75) Inventor: Anthony DiLeo, Westford, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,386

(22) Filed: Oct. 17, 2011

(65) Prior Publication Data
US 2012/0031839 A1 Feb. 9, 2012

Related U.S. Application Data

(60) Division of application No. 12/969,677, filed on Dec. 16, 2010, which is a continuation of application No. 12/455,000, filed on May 27, 2009, now Pat. No. 7,901,627, which is a division of application No. 11/402,437, filed on Apr. 12, 2006, now abandoned.

(51) Int. Cl.
*G01N 1/18* (2006.01)

(52) U.S. Cl. ............ 436/177; 436/3; 436/149; 436/164; 422/119; 422/68.1; 422/82.05; 422/82.06; 422/82.07; 422/82.08; 422/82.09; 422/82.11; 422/83; 435/283.1; 435/287.1; 435/287.8; 435/287.9; 435/288.7; 210/178; 210/198.1; 210/636; 210/639; 210/650; 210/652; 210/739; 210/741; 210/85; 210/90; 210/304; 210/512.1; 250/302; 250/343; 324/663; 324/698; 702/188; 702/50; 702/190; 73/61.63; 73/61.69; 73/114.77; 73/38; 73/40.7; 73/7; 73/861.42

(58) Field of Classification Search .............. 436/3, 149, 436/164, 177; 422/119, 68.1, 82.05, 82.06, 422/82.07, 82.08, 82.09, 82.11, 83; 435/283.1, 435/287.1, 287.2, 287.7, 287.8, 287.9, 288.7, 435/295.3, 297.1, 297.3; 210/178, 198.1, 210/304, 512.1, 636, 639, 650, 652, 739, 210/741, 788, 905, 85, 90; 250/302, 343; 324/663, 698; 702/188, 50, 190; 73/61.63, 73/61.69, 114.77, 38, 40.7, 7, 861.42
See application file for complete search history.

(56) References Cited

U.S. PATENT DOCUMENTS 2,131,509 A 9/1938 Goepel et al.
(Continued)

FOREIGN PATENT DOCUMENTS

CN 1619277 A 5/2005
(Continued)

OTHER PUBLICATIONS

European Communication dated Mar. 25, 2010 in co-pending foreign application EP 08153281.4.
(Continued)

*Primary Examiner* — Dennis M White
(74) *Attorney, Agent, or Firm* — Nields, Lemack & Frame, LLC

(57) ABSTRACT

The present invention describes a system and method for accurately measuring the concentration of a substance within a filter housing. A concentration sensor and a communications device are coupled so as to be able to measure and transmit the concentration of a particular substance within the filter housing while in use. This system can comprise a single component, integrating both the communication device and the concentration sensor. Alternatively, the system can comprise separate sensor and transmitter components, in communication with one another. In yet another embodiment, a storage element can be added to the system, thereby allowing the device to store a set of concentration values. The use of this device is beneficial to many applications. For example, the ability to read concentration values in situ allows integrity tests to be performed without additional equipment.

5 Claims, 1 Drawing Sheet

Temperature Probe / RFID
Communication Device within Filter Endcap

U.S. PATENT DOCUMENTS

| | | | |
|---|---|---|---|
| 3,698,556 | A | 10/1972 | Emmett, Jr. et al. |
| 3,877,893 | A | 4/1975 | Sweny et al. |
| 4,052,176 | A | 10/1977 | Child et al. |
| 4,211,075 | A | 7/1980 | Ludecke et al. |
| 4,272,109 | A | 6/1981 | Ahlstone |
| 4,552,572 | A | 11/1985 | Galstaun |
| 4,568,364 | A | 2/1986 | Galstaun et al. |
| 4,840,648 | A | 6/1989 | Grunewald et al. |
| 4,957,515 | A | 9/1990 | Hegarty |
| 5,040,805 | A | 8/1991 | Ozora |
| 5,121,929 | A | 6/1992 | Cobb |
| 5,240,476 | A | 8/1993 | Hegarty |
| 5,240,612 | A | 8/1993 | Grangeon et al. |
| 5,246,235 | A | 9/1993 | Heinzen |
| 5,256,294 | A | 10/1993 | van Reis |
| 5,367,910 | A | 11/1994 | Woodward et al. |
| 5,476,592 | A | 12/1995 | Simard |
| 5,540,448 | A | 7/1996 | Heinzen |
| 5,560,278 | A | 10/1996 | Lark |
| 5,581,017 | A | 12/1996 | Bejtlich, III |
| 5,581,019 | A | 12/1996 | Minor et al. |
| 5,624,537 | A | 4/1997 | Turner et al. |
| 5,674,381 | A | 10/1997 | Den Dekker |
| 5,683,119 | A | 11/1997 | Emmons et al. |
| 5,786,528 | A | 7/1998 | Dileo et al. |
| 5,947,689 | A | 9/1999 | Schick |
| 6,003,872 | A | 12/1999 | Nord |
| 6,077,435 | A | 6/2000 | Beck et al. |
| 6,090,187 | A | 7/2000 | Kumagai |
| 6,090,356 | A | 7/2000 | Jahnke et al. |
| 6,265,973 | B1 | 7/2001 | Brammall et al. |
| 6,296,770 | B1 | 10/2001 | Wilcox et al. |
| 6,333,699 | B1 | 12/2001 | Zierolf |
| 6,350,382 | B1 | 2/2002 | Schick |
| 6,365,395 | B1 | 4/2002 | Antoniou |
| 6,471,853 | B1 | 10/2002 | Moscaritolo |
| 6,485,703 | B1 | 11/2002 | Cote et al. |
| 6,595,523 | B1 | 7/2003 | Heinzen |
| 6,615,639 | B1 | 9/2003 | Heinzen |
| 6,649,829 | B2 | 11/2003 | Garber et al. |
| 6,652,740 | B2 | 11/2003 | Schoess |
| 6,694,727 | B1 | 2/2004 | Crawley et al. |
| 6,853,203 | B2 | 2/2005 | Beylich et al. |
| 6,897,374 | B2 | 5/2005 | Garber et al. |
| 6,936,160 | B2 | 8/2005 | Moscaritolo et al. |
| 6,983,504 | B2 | 1/2006 | Grummert et al. |
| 7,009,409 | B2 | 3/2006 | Davie et al. |
| 7,048,775 | B2 | 5/2006 | Jornitz et al. |
| 7,198,303 | B2 | 4/2007 | Brophy, III et al. |
| 7,264,649 | B1 | 9/2007 | Johnson et al. |
| 7,398,692 | B2 | 7/2008 | Hiroki et al. |
| 7,594,425 | B2 | 9/2009 | Lewnard et al. |
| 7,901,627 | B2 | 3/2011 | DiLeo |
| 8,007,568 | B2 | 8/2011 | DiLeo et al. |
| 2001/0006485 | A1 | 7/2001 | Kubiak et al. |
| 2001/0042684 | A1 | 11/2001 | Essalik et al. |
| 2001/0042707 | A1 | 11/2001 | Niers et al. |
| 2002/0093431 | A1 | 7/2002 | Zierolf |
| 2002/0096467 | A1 | 7/2002 | Cappia et al. |
| 2002/0144938 | A1 | 10/2002 | Hawkins et al. |
| 2003/0042688 | A1 | 3/2003 | Davie et al. |
| 2003/0047517 | A1 | 3/2003 | Schoess |
| 2003/0090390 | A1 | 5/2003 | Snider et al. |
| 2003/0116487 | A1 | 6/2003 | Petersen |
| 2003/0168408 | A1 | 9/2003 | Rajagopalan et al. |
| 2003/0179002 | A1 | 9/2003 | Beylich et al. |
| 2004/0079686 | A1 | 4/2004 | Moscaritolo et al. |
| 2004/0112529 | A1 | 6/2004 | Karlsson et al. |
| 2004/0130438 | A1 | 7/2004 | Garber |
| 2004/0135684 | A1 | 7/2004 | Steinthal et al. |
| 2004/0172210 | A1 | 9/2004 | Rothfuss et al. |
| 2004/0188331 | A1 | 9/2004 | Moscaritolo |
| 2004/0239521 | A1 | 12/2004 | Zierolf |
| 2004/0256328 | A1 | 12/2004 | Jornitz et al. |
| 2005/0039749 | A1 | 2/2005 | Emerson |
| 2005/0156487 | A1 | 7/2005 | Tseng et al. |
| 2005/0211934 | A1 | 9/2005 | Garber et al. |
| 2005/0224577 | A1 | 10/2005 | Rozenblat et al. |
| 2005/0247114 | A1 | 11/2005 | Kahn et al. |
| 2006/0060512 | A1 | 3/2006 | Astle et al. |
| 2006/0188994 | A1 | 8/2006 | Ding et al. |
| 2007/0193361 | A1 | 8/2007 | Coffey et al. |
| 2007/0241510 | A1 | 10/2007 | DiLeo |
| 2008/0041165 | A1 | 2/2008 | Coffey et al. |
| 2008/0258401 | A1 | 10/2008 | Cotton |
| 2009/0098021 | A1 | 4/2009 | DiLeo |
| 2009/0225808 | A1 | 9/2009 | DiLeo |
| 2011/0016953 | A1 | 1/2011 | DiLeo et al. |
| 2011/0017062 | A1 | 1/2011 | DiLeo et al. |
| 2011/0036782 | A1 | 2/2011 | DiLeo |
| 2011/0084024 | A1 | 4/2011 | DiLeo |

FOREIGN PATENT DOCUMENTS

| | | | |
|---|---|---|---|
| DE | 641246 | C | 1/1937 |
| DE | 4106080 | A1 | 6/1991 |
| DE | 20215056 | U1 | 2/2003 |
| DE | 10151270 | A1 | 5/2003 |
| EP | 0518250 | A1 | 12/1992 |
| EP | 0638798 | A1 | 2/1995 |
| EP | 0640822 | A3 | 3/1995 |
| EP | 0700313 | B1 | 11/1996 |
| EP | 1106962 | A2 | 6/2001 |
| EP | 1340976 | A1 | 9/2003 |
| EP | 1473069 | A1 | 11/2004 |
| GB | 2303082 | A | 2/1997 |
| JP | 6-67458 | A | 3/1994 |
| JP | 6-79147 | A | 3/1994 |
| JP | 9-24209 | A | 1/1997 |
| JP | 2002-519880 | A | 7/2002 |
| JP | 2002-538519 | A | 11/2002 |
| JP | 2002-539441 | A | 11/2002 |
| NL | 1020491 | C2 | 10/2003 |
| NO | 20020499 | L | 3/2002 |
| SU | 1259869 | A1 | 6/1993 |
| WO | 85/02783 | A1 | 7/1985 |
| WO | 94/11721 | A1 | 5/1994 |
| WO | 99/67851 | A1 | 12/1999 |
| WO | 00/40322 | A1 | 7/2000 |
| WO | 00/50849 | A1 | 8/2000 |
| WO | 00/54841 | A1 | 9/2000 |
| WO | 01/16030 | A1 | 3/2001 |
| WO | 02/078823 | A1 | 10/2002 |
| WO | 02/088618 | A1 | 11/2002 |
| WO | 03/037483 | A1 | 5/2003 |
| WO | 2004/016334 | A2 | 2/2004 |
| WO | 2004/082743 | A1 | 9/2004 |
| WO | 2004/085027 | A1 | 10/2004 |
| WO | 2005/031195 | A1 | 4/2005 |
| WO | 2005/091959 | A2 | 10/2005 |
| WO | 2005/102401 | A2 | 11/2005 |
| WO | 2006/026253 | A2 | 3/2006 |
| WO | 2008/008426 | A2 | 1/2008 |

OTHER PUBLICATIONS

European Search Report dated Aug. 27, 2010 in corresponding foreign application EP 10168357.

European Search Report dated Jul. 30, 2010 in co-pending foreign application EP 10168595.

European Communication dated Sep. 10, 2010 in co-pending foreign application EP 08171668.0.

Japanese communication dated Jan. 13, 2009 in co-pending foreign application JP 2007-102715.

Japanese Communication dated Mar. 16, 2010 in co-pending foreign application JP 2007-101613.

Japanese Communication dated May 11, 2010 in co-pending foreign application JP 2007-102696.

Japanese Communication dated Jun. 15, 2010 in co-pending foreign application JP 2007-100632.

Office Action dated May 20, 2009 in co-pending U.S. Appl. No. 11/402,737.

Office Action dated Sep. 23, 2009 in co-pending U.S. Appl. No. 11/402,737.

Office Action dated Mar. 12, 2010 in co-pending U.S. Appl. No. 11/402,737.

Office Action dated Aug. 20, 2010 in co-pending U.S. Appl. No. 11/402,737.
Office Action dated Jan. 20, 2010 in co-pending U.S. Appl. No. 12/454,092.
Office Action dated May 6, 2010 in co-pending U.S. Appl. No. 12/454,092.
Office Action dated Nov. 22, 2010 in co-pending U.S. Appl. No. 12/454,092.
Office Action dated Dec. 10, 2010 in co-pending U.S. Appl. No. 12/703,246.
Final Rejection dated Jan. 27, 2011 in co-pending U.S. Appl. No. 12/703,246.
Office Action dated Feb. 25, 2009 in corresponding U.S. Appl. No. 11/402,437.
Final Rejection dated Sep. 29, 2009 in corresponding U.S. Appl. No. 11/402,437.
Office Action dated Feb. 19, 2010 in corresponding U.S. Appl. No. 11/402,437.
Office Action dated Jul. 23, 2009 in corresponding U.S. Appl. No. 12/315,683.
Office Action dated Mar. 4, 2010 in corresponding U.S. Appl. No. 12/315,683.
Office Action Nov. 10, 2010 in corresponding U.S. Appl. No. 12/315,683.
Office Action Nov. 9, 2009 in corresponding U.S. Appl. No. 12/455,000.
Office Action dated Jun. 29, 2010 in corresponding U.S. Appl. No. 12/455,000.
Notice of Allowance dated Dec. 3, 2010 in corresponding U.S. Appl. No. 12/455,000.
Office Action dated Aug. 3, 2009 in co-pending U.S. Appl. No. 11/402,438.
Office Action dated Jan. 13, 2010 in co-pending U.S. Appl. No. 11/402,438.
Office Action dated Apr. 23, 2010 in co-pending U.S. Appl. No. 11/402,438.
Office Action dated Aug. 10, 2010 in co-pending U.S. Appl. No. 11/402,438.
Office Action dated Oct. 12, 2010 in co-pending U.S. Appl. No. 11/402,438.
Office Action dated Jan. 18, 2011 in co-pending U.S. Appl. No. 12/894,652.
Office Action dated Jan. 18, 2011 in co-pending U.S. Appl. No. 12/894,685.
Office Action dated Feb. 14, 2011 in co-pending U.S. Appl. No. 12/969,153.
Office Action dated Sep. 1, 2009 in co-pending U.S. Appl. No. 11/402,530.
Office Action dated Mar. 16, 2010 in co-pending U.S. Appl. No. 11/402,530.
Office Action dated Dec. 27, 2010 in co-pending U.S. Appl. No. 12/901,547.
Office Action dated Feb. 28, 2011 in co-pending U.S. Appl. No. 12/984,145.
Office Action dated Mar. 1, 2011 in corresponding U.S. Appl. No. 12/315,683.
Millipore Publication, 1999, pp. 1-12, "Filter Integrity Test Methods".
Office Action dated Mar. 9, 2011 in co-pending U.S. Appl. No. 12/984,155.
Final Rejection dated Mar. 9, 2011 in oo-pending U.S. Appl. No. 11/402,737.
Office Action dated Mar. 23, 2011 in co-pending U.S. Appl. No. 12/984,341.
Final Rejection dated Jun. 3, 2011 in co-pending U.S. Appl. No. 12/894,652.
Final Rejection dated Jun. 2, 2011 in co-pending U.S. Appl. No. 12/969,153.
Sunshine, "Passive Chemical Sensor", U.S. Appl. No. 60/477,624, Jun. 10, 2003, pp. 1-13.
Final Rejection dated Apr. 21, 2011 in co-pending U.S. Appl. No. 12/901,547.
Office Action dated Apr. 19, 2011 in corresponding U.S. Appl. No. 12/898,134.
Notice of Allowance dated Apr. 28, 2011 in co-pending U.S. Appl. No. 11/402,438.
Final Rejection dated May 2, 2011 in co-pending U.S. Appl. No. 12/894,685.
Millipore Publication, 2003, pp. 1-4, "Steam in Place Method for Millipore Express SHF Filters".
Pharmaceutical Technology (Supplement), Filtration for Aseptic Processing—a Tech. Primer, Oct. 2004, pp. 1-4, "Principles of Steam-In-Place", CAPPIA.
Journal of Membrane Science, V. 130 (1997), pp. 123-140, "Constant C-wall ultrafiltration process control", Van Reis, et al.
Chinese Communication dated Feb. 6, 2009 in corresponding foreign application CN 200710096550.8.
Chinese Communication dated Feb. 6, 2009 in co-pending foreign application CN 200710096545.7.
Chinese Communication dated Apr. 17, 2009 in co-pending foreign application CN 200710096551.2.
Chinese Communication dated Apr. 17, 2009 in co-pending foreign application CN200710096800.8.
European Communication dated Jul. 23, 2007 in co-pending foreign application EP 07251310.4.
European Communication dated Jul. 24, 2007 in co-pending foreign application EP 07251311.2.
European Communication dated Oct. 30, 2007 in co-pending foreign application EP 07251310.4.
European Communication dated Nov. 12, 2007 in co-pending foreign application EP 07251312.0.
European Communication dated Mar. 28, 2008 in co-pending foreign application EP 07251312.0.
European Communication dated May 26, 2008 in co-pending foreign application EP 08153280.6.
European Communication dated May 26, 2008 in co-pending foreign application EP 08153281.4.
European Communication dated Jan. 16, 2009 in co-pending foreign application EP 08171668.0.
European Communication dated Nov. 27, 2009 in co-pending foreign application EP 08162711.9.
European Communication dated Feb. 3, 2010 in co-pending foreign application EP 07251310.4.
European Communication dated Feb. 2, 2010 in co-pending foreign application EP 07251311.2.
European Search Report and Written Opinion dated Oct. 5, 2011 in co-pending European Patent Application No. EP 10179261.2.
Office Action mailed Nov. 22, 2011 in co-pending U.S. Appl. No. 12/454,092.
Notice of Allowance dated Oct. 17, 2011 in corresponding U.S. Appl. No. 12/315,683.
Office Action (Restriction) dated Sep. 16, 2011 in corresponding U.S. Appl. No. 12/969,677.
Notice of Allowance dated Jul. 6, 2011 in co-pending U.S. Appl. No. 11/402,438.
Final Rejection dated Aug. 19, 2011 in co-pending U.S. Appl. No. 12/984,341.
Office Action dated Sep. 23, 2011 in co-pending U.S. Appl. No. 13/164,988.
Final Rejection dated Aug. 9, 2011 in co-pending U.S. Appl. No. 12/984,145.
Office Action dated Aug. 19, 2011 in co-pending U.S. Appl. No. 13/164,894.
Final Rejection dated Jul. 14, 2011 in co-pending U.S. Appl. No. 12/984,155.

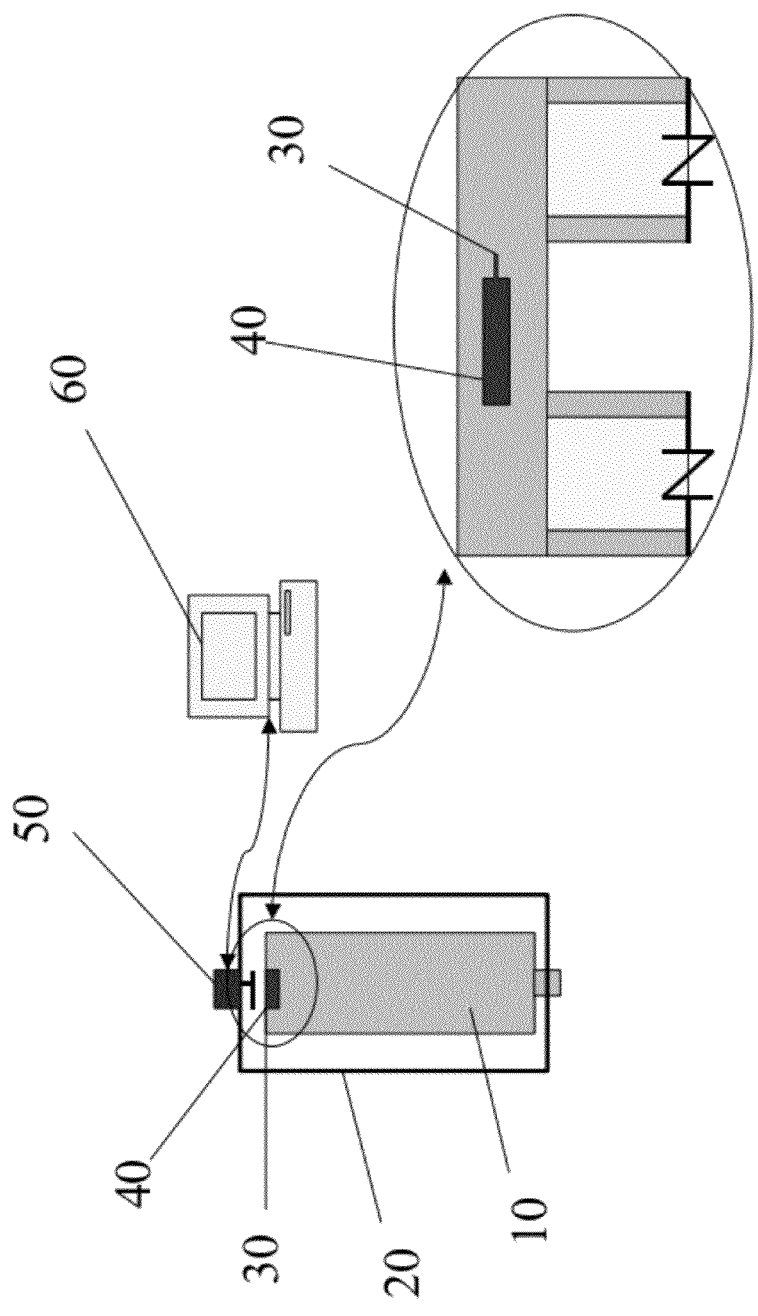
Figure 1: Temperature Probe / RFID Communication Device within Filter Endcap

METHOD OF MAINTAINING A PROTEIN CONCENTRATION AT A TANGENTIAL FLOW FILTER

This application is a divisional application of U.S. patent application Ser. No. 12/969,677, filed Dec. 16, 2010, which is a continuation application of U.S. patent application Ser. No. 12/455,000, filed May 27, 2009, which issued as U.S. Pat. No. 7,901,627, which is a divisional application of U.S. patent application Ser. No. 11/402,437, filed Apr. 12, 2006, the disclosures of which are incorporated herein by reference in their entireties.

BACKGROUND OF THE INVENTION

The use of wireless communication has become prevalent, especially in the management of assets, particularly those applications associated with inventory management. For example, the use of RFID tags permits the monitoring of the production line and the movement of assets or components through the supply chain.

To further illustrate this concept, a manufacturing entity may adhere RFID tags to components as they enter the production facility. These components are then inserted into the production flow, forming sub-assemblies in combination with other components, and finally resulting in a finished product. The use of RFID tags allows the personnel within the manufacturing entity to track the movement of the specific component throughout the manufacturing process. It also allows the entity to be able to identify the specific components that comprise any particular assembly or finished product.

In addition, the use of RFID tags has also been advocated within the drug and pharmaceutical industries. In February 2004, the United States Federal and Drug Administration issued a report advocating the use of RFID tags to label and monitor drugs. This is an attempt to provide pedigree and to limit the infiltration of counterfeit prescription drugs into the market and to consumers.

Since their introduction, RFID tags have been used in many applications, such as to identify and provide information for process control in filter products. U.S. Pat. No. 5,674,381, issued to Den Dekker in 1997, discloses the use of "electronic labels" in conjunction with filtering apparatus and replaceable filter assemblies. Specifically, the patent discloses a filter having an electronic label that has a read/write memory and an associated filtering apparatus that has readout means responsive to the label. The electronic label is adapted to count and store the actual operating hours of the replaceable filter. The filtering apparatus is adapted to allow use or refusal of the filter, based on this real-time number. The patent also discloses that the electronic label can be used to store identification information about the replaceable filter.

A patent application by Baker et al, published in 2005 as U.S. Patent Application Publication No. US2005/0205658, discloses a process equipment tracking system. This system includes the use of RFID tags in conjunction with process equipment. The RFID tag is described as capable of storing "at least one trackable event". These trackable events are enumerated as cleaning dates, and batch process dates. The publication also discloses an RFID reader that is connectable to a PC or an internet, where a process equipment database exists. This database contains multiple trackable events and can supply information useful in determining "a service life of the process equipment based on the accumulated data". The application includes the use of this type of system with a variety of process equipment, such as valves, pumps, filters, and ultraviolet lamps.

Another patent application, filed by Jornitz et al and published in 2004 as U.S. Patent Application Publication No. 2004/0256328, discloses a device and method for monitoring the integrity of filtering installations. This publication describes the use of filters containing an onboard memory chip and communications device, in conjunction with a filter housing. The filter housing acts as a monitoring and integrity tester. That application also discloses a set of steps to be used to insure the integrity of the filtering elements used in multi-round housings. These steps include querying the memory element to verify the type of filter that is being used, its limit data, and its production release data.

Despite the improvements that have occurred through the use of RFID tags, there are additional areas that have not been satisfactorily addressed. For example, there are a number of applications, such as integrity testing and protein monitoring, in which real time monitoring of the concentration of a particular substance would be extremely beneficial. While RFID tags offer one embodiment of the present invention, solutions utilizing wired communication are also envisioned.

SUMMARY OF THE INVENTION

The shortcomings of the prior art are overcome by the present invention, which describes a system and method for accurately measuring the concentration of a substance within a filter element. In certain embodiments, a sensor, capable of measuring the concentration of a particular substance, and a communications device are coupled so as to be able to measure and transmit the concentration of a particular substance in the vicinity of a filter, while in use. This system can comprise a single component, integrating both the communication device and the sensor. Alternatively, the system can comprise separate sensor and transmitter components, in communication with one another. In yet another embodiment, a storage element can be added to the system, thereby allowing the device to store a set of concentration values. In yet another embodiment, the transmitter components operate wirelessly.

The use of this device is beneficial to many applications. For example, a newly developed integrity test is based on the concept of adding a tracer gas to a carrier. Detection of this tracer gas gives higher sensitivity than a standard diffusion test. The ability to detect this gas and transmit the results outside the filter housing would be greatly beneficial. In another application, the ability to monitor the protein concentration within the filter housing enables the operating conditions to be adjusted so as to maintain the protein concentration at the membrane surface for more reliable and reproducible performance.

BRIEF DESCRIPTION OF THE DRAWINGS

FIG. 1 is a representative embodiment of the present invention.

DETAILED DESCRIPTION OF THE INVENTION

FIG. 1 illustrates a representative filtering system in accordance with the present invention. The filter element 10 is enclosed with a housing 20. The filter element can be simply a porous material, such as pleated paper. Alternatively, the filter element may be more complex; for example, comprising a frame, such as of plastic, and a porous material. Located in close proximity of, and preferably affixed to, the filter element 10 is a concentration sensor 30. This sensor 30 is capable of generating an output, which varies as a function of the surrounding concentration of a particular substance. This output can be in the form of an analog voltage or current, or can be a digital value or pulse. In the preferred embodiment, the output varies linearly with the concentration, however this is not a requirement. Any output having a known relationship, such as logarithmic or exponential, to the surrounding concentration, can be employed. In such a situation, a transformation of the output can be performed to determine the actual measured concentration.

The concentration sensor 30 is preferably mounted on the downstream side of the filter element 10. In applications where the concentration of interest is homogeneous, the location of sensor 30 is not critical, and can be anywhere on the downstream side of the filter element, such as, but not limited to, the inner surface of the filter element or in the common outlet. In those applications where the concentration is discrete and non-homogeneous, the concentration sensor may be located in proximity to the output of the filter element. In other embodiments, the concentration sensor 30 can be located within the common outlet. In some applications, the temperature of the filter element may exceed 145° C., therefore a sensor capable of withstanding this temperature should be employed. Similarly, the temperature with the housing 20 may cycle from lower temperatures to higher temperatures and back, therefore the sensor should be able to withstand temperature cycling. There are multiple embodiments of this concentration sensor. For example, in certain applications, this sensor is a solid state device that uses a particular compound known to interact with the desired gas. In one embodiment of a hydrogen sensor, a MOS diode is used, where the metal alloy layer comprises a PdAg alloy, the oxide in $SiO_2$ and the semiconductor is silicon. Hydrogen affects the junction between the metal and oxide layers, thereby changing the characteristics of the diode. This junction variation can then be translated into a concentration level. In another embodiment, a metal oxide semiconductor thick film device where the oxide is $SnO_2$ is utilized. The presence of oxidizing gases near the sensor changes the resistance characteristics of the device, thereby allowing the concentration of the gas to be determined. Alternatively, other sensors utilize infrared (IR) dispersion to detect particular substances. In these sensors, a beam of IR is transmitted toward a receiver. The particular substance of interest, such as a gas, absorbs some of the IR radiation as it passes from the transmitter to the receiver. The amount of absorption is related to the concentration of the substance. IR and UV light can also be used, typically in conjunction with a fiber optic cable, to measure solute concentration through the use of refraction. Another type of sensor is an affinity-based sensor based on an optical, electrical or piezoelectric detection methodology. One such affinity-based sensor utilizes a microbalance on which a suitable ligand is placed. The substance in question is attached to and adheres to the ligand. This results in a small increase in the mass located on the microbalance. This mass can then be converted to a concentration rate, based on flow rate. These examples are intended to be illustrative of some of the types of sensors that can be used; this is not intended to be an exhaustive list of all such suitable concentration sensors.

A transmitter 40 is also located near, or integrated with, the sensor 30. In the preferred embodiment, the transmitter 40 and the concentration sensor 30 are encapsulated in a single integrated component. Alternatively, the transmitter 40 and the sensor 30 can be separated, and in communication with each other, such as via electrical signals. Various types of communication devices are possible. In one embodiment, wireless communication is used, and the use of an RFID tag is preferred. An active RFID tag allows regular communication with the reader. Alternatively, a passive RFID tag can be used, whereby the energy to transmit and sense the temperature is obtained from the electromagnetic field transmitted by the RFID reader. In another embodiment, wired communication between the sensor and a control module outside the housing is used.

Optionally, a storage element 50 can be used in conjunction with the transmitter 40 and the concentration sensor 30. This storage element 50, which is preferably a random access memory (RAM) or FLASH EPROM device, can be used to store a set of concentration readings, such as may be generated by regular sampling of the sensor.

This allows the rate at which the transmitter 40 sends data to be different from the rate at which the concentration is sampled. For example, the concentration may be sampled 10 times per second, while the data is transmitted only once per second.

In one embodiment, a wireless receiver, 60, located outside the filter housing 20, is used to communicate with the transmitter. In the preferred embodiment, an RFID reader or base station is used. The reader can be configured such that it queries the transmitter at regular intervals. Alternatively, the reader can be manually operated so that readings are made when requested by the equipment operator. In another embodiment, the wireless receiver 60 also includes a storage element. This reduces the complexity required of the device within the housing. In this embodiment, the wireless receiver queries the wireless transmitter/concentration sensor at preferably regular intervals. It receives from the wireless transmitter the current concentration sensor measurement as determined at that time. The wireless receiver 60 then stores this value in its storage element. The capacity of the storage element can vary, and can be determined based on a variety of factors. These include, but are not limited to, the rate at which measurements are received, the rate at which the stored data is processed, and the frequency with which this storage element is in communication with its outside environment.

As an example, consider a filter element having a wireless transmitter 40, such as an RFID tag, coupled with a concentration sensor 30. In this embodiment, the RFID tag is passive, that is, it only sends data upon receipt of a query from the wireless receiver, or base station. Upon receipt of that query, the transmitter transmits the value currently available from the concentration sensor 30. In one scenario, the wireless receiver, which is coupled to a computing device, such as a computer, then stores these values, optionally with an associated timestamp, such as in a log file. In a different scenario, if the wireless receiver is separated from the computer, the receiver will need to store a number of concentration measurements internally, until such time as it is connected to the main computing and/or storage device. In this case, a storage element needs to be integrated with the receiver.

Mechanisms for transmitting wireless signals outside the housing have been disclosed and are known in the art. United States Patent Application Publication 2004/0256328 describes the use of an antenna to relay information between transponders located on the filter housing to a monitoring and test unit external to the housing.

Having defined the physical structure of the present invention, there are a number of applications in which it is beneficial. The following is meant to illustrate some of those applications, however it is not intended as a recitation of all such applications.

In one embodiment, the present invention is used in conjunction with in situ Integrity Testing. This process allows the operator to certify the integrity of the filters within the filter housing at the customer site without additional equipment. In one embodiment, a tracer gas, such as helium or hydrogen, is added to a carrier and injected into the system. A sensor, preferably a solid state gas sensor capable of measuring concentrations of the tracer gas, is preferably positioned on the downstream side of the filter, so as to measure the breakthrough of the tracer gas. The sensor can optionally be protected by a hydrophobic filter to avoid fouling with protein and other materials. The concentration of tracer gas at a specific operating transmembrane pressure is indicative of bubble pointing specific pores in the filter. The concentration of tracer gas indicates the filter's integrity, and thus, pass/fail criteria can be established for each filter type. This test will give a more sensitive indication of the bubble point and the presence of defects than a standard diffusion test. This test is applicable to any filter, but is most ideally suited to Normal Flow Parvovirus (NFP) filters.

In a second embodiment, two gasses, in a known ratio, are introduced into the filter housing. This embodiment is described in greater detail in U.S. Provisional Application Ser. No. 60/725,238, filed Oct. 11, 2005. In the preferred embodiment, the filter element is wetted with a suitable liquid, and the selected gasses have different permeability in that liquid. The gasses used can be of various compositions, including noble gasses, perfluorinated gasses, or carbon dioxide. Because of the difference in permeability, the gasses diffuse through the filter element at different rates, thereby creating a different ratio on the downstream side of the filter element. Based on this ratio, the integrity of the filter element can be verified. The use of one or more concentration sensors permits the monitoring of this downstream ratio.

A second application of the present invention relates to protein monitoring. In this scenario, a sensor capable of measuring solute concentration, most preferably protein concentration, is used to control the filtration processes. In this application, the sensor is preferably either an optical fiber through which an ultraviolet or infrared measurement can be made; an affinity based sensor based on an optical, electrical or piezoelectric detection method or an affinity-based sensor using a microbalance and suitable ligand. In tangential flow filtration (TFF) applications, the sensor is located on the filter, preferably at the membrane surface physically integral with the filter at the outlet end of the flow channel. The sensor is then capable of measuring the protein concentration at the membrane surface. Based on this reading, operating conditions, such as transmembrane pressure, can be adjusted so as to maintain the protein concentration at a particular level. This type of control is particularly well suited for tangential flow filtration where a concentration boundary layer is built on top of the filter membrane. The membrane performance, both flux and sieving, is determined by the wall concentration of the deposited protein. Thus, by varying transmembrane pressure, the concentration of protein at the membrane wall can be kept within a specified window.

In operation, the sensor 30 measures the concentration. This value is then communicated outside of the filter housing by the transmitter 40. The external receiver 60 receives this measured concentration value. Using a conventional control loop employing an algorithm, such as proportional-integral-derivative (PID) or proportional-derivative (PD), an updated desired transmembrane pressure can be calculated based on the current pressure and the received concentration measurement. This new value is then applied to the system. By dynamically adjusting the pressure, batch-to-batch variations can be easily accommodated.

In one embodiment, a plastic filter housing is utilized, allowing the wireless transmitter to transmit pressure data through the housing at any time.

What is claimed is:

1. A method of maintaining a protein concentration at the membrane surface of a tangential flow filtering element within a filter housing, comprising:
   attaching a concentration sensor to the membrane surface of said filtering element;
   monitoring the concentration of said protein using said sensor;
   comparing said concentration to a predetermined range; and
   adjusting the transmembrane pressure in response to said comparison.

2. The method of claim 1, wherein said concentration sensor is in communication with a transmitter, further comprising the step of transmitting said monitored concentration to a receiver located outside of said housing said transmitter.

3. The method of claim 2, wherein said transmitter utilizes wireless communication.

4. The method of claim 3, wherein said wireless transmitter comprises an RFID tag.

5. The method of claim 1, wherein said adjustment is calculated using a PID loop.

* * * * *